(12) United States Patent
Croft

(10) Patent No.: US 11,620,464 B2
(45) Date of Patent: Apr. 4, 2023

(54) IN-VIVO INTRODUCIBLE ANTENNA FOR DETECTION OF RF TAGS

(71) Applicant: Covidien LP, Mansfield, MA (US)

(72) Inventor: Richard L. Croft, Mead, CO (US)

(73) Assignee: COVIDIEN LP, Mansfield, MA (US)

( * ) Notice: Subject to any disclaimer, the term of this patent is extended or adjusted under 35 U.S.C. 154(b) by 66 days.

(21) Appl. No.: 17/188,670

(22) Filed: Mar. 1, 2021

(65) Prior Publication Data

US 2021/0303808 A1 Sep. 30, 2021

Related U.S. Application Data

(60) Provisional application No. 63/002,487, filed on Mar. 31, 2020.

(51) Int. Cl.
| | | |
|---|---|---|
| *G06K 7/10* | (2006.01) | |
| *G06K 19/077* | (2006.01) | |
| *H01Q 1/22* | (2006.01) | |
| *H01Q 7/00* | (2006.01) | |

(52) U.S. Cl.
CPC ... *G06K 7/10386* (2013.01); *G06K 19/07758* (2013.01); *G06K 19/07775* (2013.01); *H01Q 1/2208* (2013.01); *H01Q 7/00* (2013.01)

(58) Field of Classification Search
CPC ....... G06K 19/07758; G06K 19/07775; H01Q 1/2208
USPC .......................................... 235/492
See application file for complete search history.

(56) References Cited

U.S. PATENT DOCUMENTS

| | | |
|---|---|---|
| 2,740,405 A | 4/1956 | Riordan |
| 3,422,816 A | 1/1969 | Robinson et al. |
| 3,587,583 A | 6/1971 | Greenberg |
| 4,114,601 A | 9/1978 | Abels |
| 4,193,405 A | 3/1980 | Abels |

(Continued)

FOREIGN PATENT DOCUMENTS

| | | |
|---|---|---|
| AU | 2003249257 A1 | 2/2004 |
| EP | 1612554 A1 | 1/2006 |

(Continued)

OTHER PUBLICATIONS ip.com search.*

(Continued)

*Primary Examiner* — Allyson N Trail
(74) *Attorney, Agent, or Firm* — Carter, DeLuca & Farrell, LLP

(57) ABSTRACT

An interrogation and detection system for detection of surgical implements within a patient's body, the system including One or more RFID tags affixed to a surgical implement within the patient's body. Each RFID tag being configured to transmit a return signal when energized, and a remote signal generator configured to generate an energizing signal for the one or more RFID tags. The signal generator operably coupled to the in-vivo introducible antenna via a communication cable. The system further includes an in-vivo introducible antenna configured to be inserted through a trocar-cannula assembly into a surgical site within the patient's body. Wherein the tubular channel defines a shape having a dimension "D1", such that the dimension "D1" of the tubular channel is less than the dimension "D2" of the in-vivo introducible antenna.

19 Claims, 5 Drawing Sheets

(56) References Cited

U.S. PATENT DOCUMENTS

| | | | |
|---|---|---|---|
| 4,422,548 A | 12/1983 | Cheesman et al. |
| 4,658,818 A | 4/1987 | Miller, Jr. et al. |
| 4,681,111 A | 7/1987 | Silvian |
| 4,893,118 A | 1/1990 | Lewiner et al. |
| 5,031,642 A | 7/1991 | Nosek |
| 5,057,095 A | 10/1991 | Fabian |
| 5,105,829 A | 4/1992 | Fabian et al. |
| 5,107,862 A | 4/1992 | Fabian et al. |
| 5,188,126 A | 2/1993 | Fabian et al. |
| 5,190,059 A | 3/1993 | Fabian et al. |
| 5,235,326 A | 8/1993 | Beigel et al. |
| 5,258,742 A | 11/1993 | Soldevila Domingo et al. |
| 5,329,944 A | 7/1994 | Fabian et al. |
| 5,353,011 A | 10/1994 | Wheeler et al. |
| 5,446,447 A | 8/1995 | Carney et al. |
| 5,456,718 A | 10/1995 | Szymaitis |
| 5,482,036 A | 1/1996 | Diab et al. |
| 5,629,498 A | 5/1997 | Pollock et al. |
| 5,650,596 A | 7/1997 | Morris et al. |
| 5,664,582 A | 9/1997 | Szymaitis |
| 5,886,672 A | 3/1999 | Brune et al. |
| 5,923,001 A | 7/1999 | Morris et al. |
| 5,928,151 A | 7/1999 | Hossack et al. |
| 6,026,818 A | 2/2000 | Blair et al. |
| 6,211,666 B1 | 4/2001 | Acker |
| 6,215,437 B1 | 4/2001 | Schurmann et al. |
| 6,223,137 B1 | 4/2001 | McCay et al. |
| 6,232,878 B1 | 5/2001 | Rubin |
| 6,270,460 B1 | 8/2001 | McCartan et al. |
| 6,349,234 B2 | 2/2002 | Pauly et al. |
| 6,359,562 B2 | 3/2002 | Rubin |
| 6,366,206 B1 | 4/2002 | Ishikawa et al. |
| 6,401,722 B1 | 6/2002 | Krag |
| 6,557,752 B1 | 5/2003 | Yacoob |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,240 B2 | 11/2003 | Lee et al. |
| 6,696,954 B2 | 2/2004 | Chung |
| 6,734,795 B2 | 5/2004 | Price |
| 6,777,623 B2 | 8/2004 | Ballard |
| 6,786,405 B2 | 9/2004 | Wiedenhoefer |
| 6,812,842 B2 | 11/2004 | Dimmer |
| 6,822,570 B2 | 11/2004 | Dimmer et al. |
| 6,838,990 B2 | 1/2005 | Dimmer |
| 6,861,954 B2 | 3/2005 | Levin |
| 6,879,300 B2 | 4/2005 | Rochelle et al. |
| 6,909,366 B1 | 6/2005 | Marsh et al. |
| 6,977,504 B2 | 12/2005 | Wright et al. |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,098,793 B2 | 8/2006 | Chung |
| 7,098,866 B2 | 8/2006 | Desjeux et al. |
| 7,135,978 B2 | 11/2006 | Gisselberg et al. |
| 7,142,815 B2 | 11/2006 | Desjeux et al. |
| 7,158,030 B2 | 1/2007 | Chung |
| 7,158,754 B2 | 1/2007 | Anderson |
| 7,160,258 B2 | 1/2007 | Imran et al. |
| 7,176,798 B2 | 2/2007 | Dimmer et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| 7,319,396 B2 | 1/2008 | Homanfar et al. |
| 7,319,397 B2 | 1/2008 | Chung et al. |
| 7,325,723 B2 | 2/2008 | Desjeux |
| 7,342,497 B2 | 3/2008 | Chung et al. |
| 7,362,228 B2 | 4/2008 | Nycz et al. |
| 7,382,255 B2 | 6/2008 | Chung |
| 7,397,364 B2 | 7/2008 | Govari |
| D577,421 S | 9/2008 | Williams |
| 7,420,468 B2 | 9/2008 | Fabian et al. |
| 7,423,535 B2 | 9/2008 | Chung et al. |
| 7,464,713 B2 | 12/2008 | Fabian et al. |
| 7,492,257 B2 | 2/2009 | Tethrake et al. |
| 7,508,303 B2 | 3/2009 | Capowski et al. |
| 7,513,425 B2 | 4/2009 | Chung |
| 8,111,162 B2 | 2/2012 | Barnes et al. |
| 8,358,212 B2 | 1/2013 | Blair |
| 10,478,101 B1* | 11/2019 | Cespedes ............ A61B 5/0002 |
| 11,185,261 B2* | 11/2021 | Saddow ............... A61B 5/742 |
| 2001/0030610 A1 | 10/2001 | Rochelle et al. |
| 2002/0032435 A1 | 3/2002 | Levin |
| 2002/0143320 A1 | 10/2002 | Levin |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0250819 A1 | 12/2004 | Blair et al. |
| 2005/0049564 A1 | 3/2005 | Fabian |
| 2005/0110640 A1 | 5/2005 | Chung |
| 2005/0177067 A1* | 8/2005 | Tracey .................. A61B 5/208 |
| | | 128/903 |
| 2006/0106368 A1 | 5/2006 | Miller et al. |
| 2006/0187044 A1 | 8/2006 | Fabian et al. |
| 2006/0202827 A1 | 9/2006 | Volpi et al. |
| 2006/0235488 A1 | 10/2006 | Nycz et al. |
| 2006/0241396 A1 | 10/2006 | Fabian et al. |
| 2006/0241399 A1 | 10/2006 | Fabian |
| 2007/0004994 A1 | 1/2007 | Sherman |
| 2007/0005141 A1 | 1/2007 | Sherman |
| 2007/0239289 A1 | 10/2007 | Cambre et al. |
| 2007/0265690 A1 | 11/2007 | Lichtenstein et al. |
| 2007/0285249 A1 | 12/2007 | Blair et al. |
| 2008/0007411 A1 | 1/2008 | Levin |
| 2008/0051746 A1 | 2/2008 | Shen-Gunther |
| 2008/0132860 A1 | 6/2008 | Smith et al. |
| 2008/0204245 A1 | 8/2008 | Blair et al. |
| 2008/0231452 A1 | 9/2008 | Levin |
| 2008/0237341 A1 | 10/2008 | Fleck et al. |
| 2008/0238677 A1 | 10/2008 | Blair et al. |
| 2008/0255635 A1* | 10/2008 | Bettesh ................. G16H 40/67 |
| | | 707/999.107 |
| 2008/0272913 A1 | 11/2008 | Barnes et al. |
| 2008/0281190 A1 | 11/2008 | Petcavich et al. |
| 2008/0296573 A1 | 12/2008 | Zmood et al. |
| 2011/0230147 A1 | 9/2011 | Schuh et al. |
| 2012/0262560 A1* | 10/2012 | Nisani .................. A61B 1/045 |
| | | 348/E7.085 |
| 2014/0273865 A1 | 9/2014 | Skarda et al. |
| 2014/0323821 A1* | 10/2014 | Manicka ............ A61B 5/0205 |
| | | 600/301 |
| 2015/0265171 A1* | 9/2015 | Seaver ................ A61B 5/6852 |
| | | 600/561 |
| 2016/0206399 A1 | 7/2016 | Blair |
| 2016/0371574 A1* | 12/2016 | Nguyen ............. G06K 17/0022 |
| 2017/0035341 A1* | 2/2017 | Nagale ................ A61B 5/6885 |
| 2017/0231572 A1* | 8/2017 | Lowery ............. A61M 16/0434 |
| | | 600/301 |
| 2018/0104008 A1* | 4/2018 | Dickhans ............... A61B 90/39 |
| 2020/0030039 A1 | 1/2020 | Yavari et al. |
| 2021/0085392 A1* | 3/2021 | Ehninger ............... A61B 18/16 |
| 2021/0100614 A1* | 4/2021 | Ehninger ............... A61B 18/16 |
| 2021/0210856 A1* | 7/2021 | Khait .................... H01Q 11/08 |

FOREIGN PATENT DOCUMENTS

| | | |
|---|---|---|
| KR | 20180130784 A | 12/2018 |
| WO | 2004008387 A1 | 1/2004 |
| WO | 2004086997 A1 | 10/2004 |
| WO | 2006060781 A1 | 6/2006 |

(56) References Cited

OTHER PUBLICATIONS

Barnes et al., "Design for a FET Based 1 MHz, 10kV Pulse Generator," Pulsed Power Conference, Digest of Technical Papers, Tenth IEEE International, 2:1335-1340, 1995.

Macario et al., "Initial Clinical Evaluation of a Handheld Device for Detecting Retained Surgical Gauze Sponges Using Radiofrequency Identification Technology," Arch. Surg., vol. 14, Jul. 2005, pp. 659-662.

Extended European Search Report issued in corresponding European Application No. 21165842.2 dated Aug. 20, 2021, 9 pages.

\* cited by examiner

IN-VIVO INTRODUCIBLE ANTENNA FOR DETECTION OF RF TAGS

CROSS-REFERENCE TO RELATED APPLICATIONS

The present application claims the benefit of and priority to U.S. Provisional Patent Application Ser. No. 63/002,487, filed on Mar. 31, 2020, the entire content of which is incorporated by reference herein.

TECHNICAL FIELD

This disclosure relates generally to interrogation and detection systems for the detection of radio-frequency (RF) tags, and more particularly, to insertable antennae for use within surgical sites.

BACKGROUND

It is often useful or important to determine whether objects associated with a surgery are present in a patient's body before completion of the surgery. Such objects may take a variety of forms. For example, the objects may take the form of instruments, for instance scalpels, scissors, forceps, hemostats, and/or clamps. Also, for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders (e.g., RFID tags) which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Direct interrogation of the surgical site, by transmitting a probing signal from within the open surgical site is a straightforward approach to reducing the effect of signal interference due to external factors. However, the size of the transmitting antenna limits the utility of this option. The minimally invasive approach to modern surgery discourages clinicians from cutting large open wounds into the body of the patient. Instead of large cuts to access treatment sites within the body, small apertures provide access points for surgical tools to be used internally. These apertures are generally too small to facilitate insertion of transmitting antennae into the treatment site for direct interrogation.

Furthermore, when trying to locate an RFID tagged item within the surgical site it is important for the antenna transmitting the probing signals and receiving the return signals to physically occupy as much space as possible, because larger antennae have a greater range of detection for return signals within the surgical site. Accordingly, it is desired to bypass external sources of signal interference by direct interrogation within the surgical site with a relatively large sizably adjustable antenna capable of passing through the small apertures generally employed in modern surgical practice.

SUMMARY

This disclosure relates to systems for detection of surgical objects and devices used in body cavities during surgery, specifically antennae to be inserted directly into a surgical site.

One aspect of the disclosure is directed to an interrogation and detection system for detection of surgical implements within a patient's body. The interrogation and detection system includes one or more RFID tags configured to transmit one or more return signals when energized, each RFID tag affixed to a surgical implement within the patient's body; a remote signal generator configured to generate an energizing signal for the one or more RFID tags; and an in-vivo introducible antenna operably coupled to the signal generator, the in-vivo introducible antenna configured to receive the one or more return signals transmitted by the one or more RFID tags when in an expanded state. Wherein the in-vivo introducible antenna is configured to a collapsed state, smaller than the expanded state, for insertion into the patient's body.

The system may further include a trocar-cannula assembly including a tubular channel configured to facilitate passage of the in-vivo introducible antenna therethrough, wherein the in-vivo introducible antenna defines a shape having a dimension "D2"; and wherein the tubular channel defines a shape having a dimension "D1", such that the dimension "D1" of the tubular channel is less than the dimension "D2" of the in-vivo introducible antenna.

The in-vivo introducible antenna may include a semi-rigid elongated member supporting a flexible loop configured to fold in on itself when passing through the tubular channel of the trocar-cannula assembly, and to unfold upon exiting the tubular channel of the trocar-cannula assembly and entering the surgical site within the patient's body.

The flexible loop may be composed of a shape memory alloy configured to automatically return to its initial shape in the absence of external forces.

The initial shape of the flexible loop portion of the in-vivo antenna may be circular.

The flexible loop may be configured to be folded inward to form an elongated oval shape while being translated distally through the tubular channel.

The flexible loop may be configured to be folded backwards to rest alongside the semi-rigid elongated member while being translated distally through the tubular channel.

The flexible loop may be configured to be folded along the axis of the semi-rigid elongated member to form a crescent-shaped profile while being translated proximally through the tubular channel.

The flexible loop may be tear drop-shaped.

The flexible loop may be larger in size than the tubular channel.

According to another aspect, a method for detecting one or more surgical implements within a patient's body is provided. The method includes pushing an in-vivo introducible antenna distally through a channel having a dimension "D1" defined within a trocar-cannula assembly and into a surgical site within the patient's body, wherein a portion of the in-vivo introducible antenna will automatically return to an original shape having a dimension "D2", such that the dimension "D1" of the tubular channel is less than the dimension "D2" of the in-vivo introducible antenna; generating an energizing signal configured to stimulate the one or more RFID tags into transmitting a return signal; transmitting the energizing signal directly into the surgical site within the patient's body through the expanded portion of the in-vivo introducible antenna; scanning for any return signals from one or more RFID tags affixed to each surgical implement placed within the patient's body before the surgery began; and alerting the clinician to the presence of the one or more RFID tags affixed to each surgical implement upon detection of the one or more return signals.

The in-vivo introducible antenna may include of a semi-rigid elongated member supporting a flexible loop, where the flexible loop is the portion of the in-vivo introducible antenna configured to automatically unfold to occupy an expanded area.

The method may further include pulling the unfolded flexible loop portion of the in-vivo introducible antenna proximally through the aperture and channel of the trocar-cannula assembly such that the unfolded flexible loop is compressed by the channel and collapses in on itself.

The compression of the flexible loop portion may facilitate complete withdrawal of the in-vivo introducible antenna from the trocar-cannula assembly.

The flexible loop portion may be circular in shape and configured to fold along an axis of the semi-rigid elongated member to form a crescent-shaped profile while being pulled proximally through the channel of the trocar-cannula assembly.

According to yet another aspect, a resizable in-vivo introducible antenna for insertion into a surgical site and detection of RFID tagged surgical implements within a patient's body is provided. The Antenna includes a semi-rigid elongated member configured to be translated through a tubular channel, wherein the tubular channel defines a shape having a dimension "D1"; and a flexible loop operably coupled to the semi-rigid member, wherein the flexible loop defines a shape with a dimension "D2", such that the dimension "D1" of the tubular channel is less than the dimension "D2" of the in-vivo introducible antenna.

The flexible loop may be composed of a shape memory alloy configured to automatically return to an initial shape in the absence of external forces.

The flexible loop may be sizably adjustable such that the flexible loop can be reshaped to conform to its surroundings.

The initial shape of the flexible loop may be a circle.

The flexible loop may be configured to be folded backwards to rest alongside the semi-rigid elongated member while being inserted into the surgical site within the patient's body.

The flexible loop may be configured to be folded along the longitudinal axis of the semi-rigid elongated member to form a crescent-shaped profile while being withdrawn from the surgical site within the patient's body.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

Various aspects of the presently disclosed in-vivo introducible antennae, RF tags, and articles containing them are described herein below with reference to the drawings, wherein.

DETAILED DESCRIPTION

In the following description, certain specific details are set forth in order to provide a thorough understanding of disclosed aspects. However, one skilled in the relevant art will recognize that aspects may be practiced without one or more of these specific details, or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
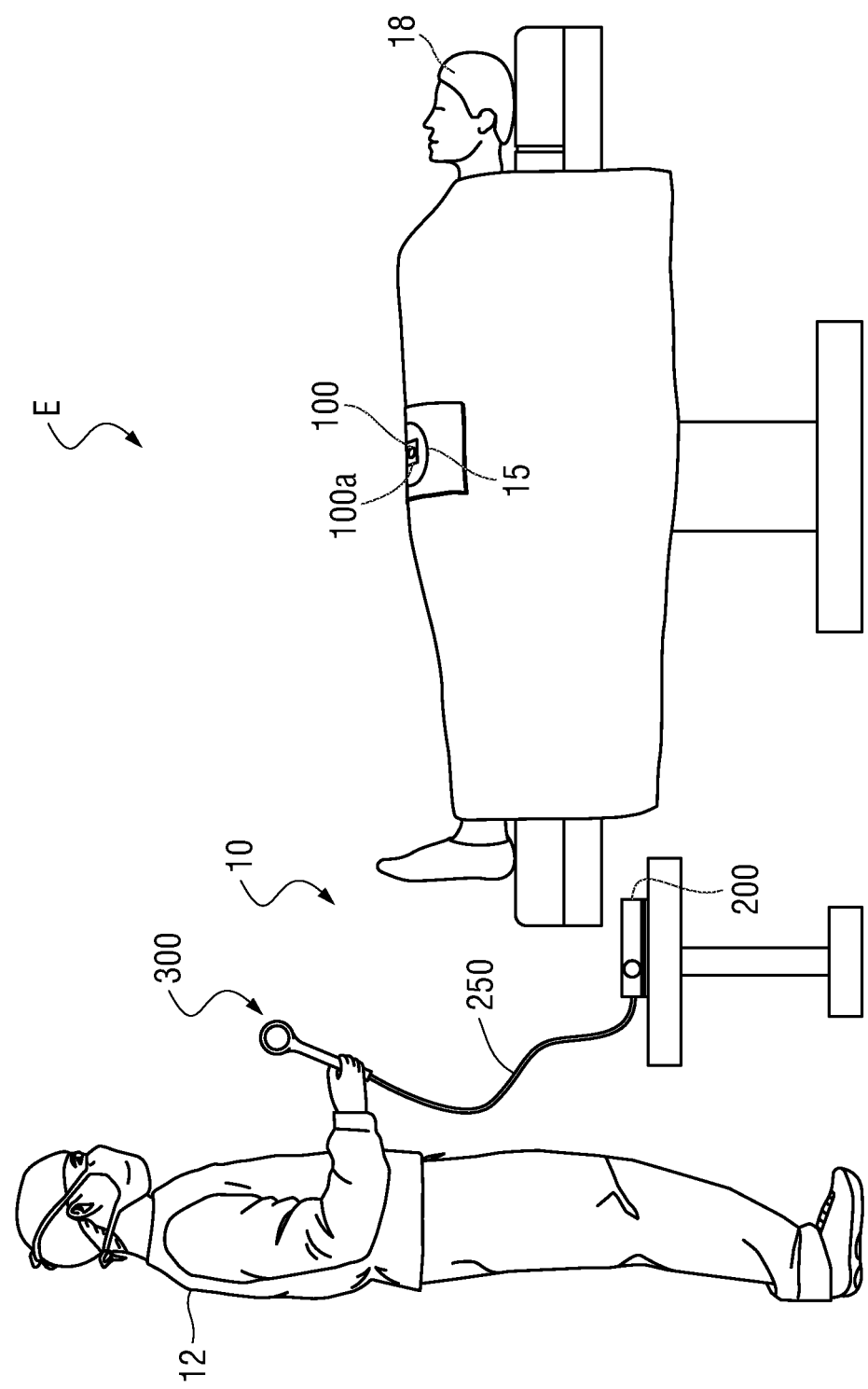
FIG. 1 is a schematic diagram showing a surgical environment illustrating a medical provider using an interrogation and detection system to detect an object within a patient that is tagged with an RFID tag according to one illustrated aspect.

FIG. 1 depicts a surgical environment "E" in which a medical provider 12 operates an interrogation and detection system 10 for detection of RFID tags to ascertain the presence or absence of objects 100a in a patient 18. The interrogation and detection system 10 may include a signal generator 200, and an antenna 300 coupled to the signal generator 200 by one or more communication paths, for example coaxial cable 250. In one aspect of the interrogation and detection system 10, the antenna 300 may take the form of a hand-held wand 300a.

The object 100a may take a variety of forms, for example instruments, accessories and/or disposable objects useful in performing surgical procedures. For instance, the object 100a may take the form of scalpels, scissors, forceps, hemostats, and/or clamps. Also for example, the objects 100a may take the form of surgical sponges, gauze and/or padding. The object 100a is tagged, carrying, attached or otherwise coupled to an RFID tag 100. Aspects of the interrogation and detection system 10 disclosed herein are particularly suited to operate with one or more RFID tags 100 which are not accurately tuned to a chosen or selected resonant frequency. Consequently, the RFID tags 100 do not require high manufacturing tolerances or expensive materials, and thus may be inexpensive to manufacture.

In use, the medical provider 12 may position the wand 300a approximate the patient 18 in order to detect the presence or absence of the one or more RFID tags 100 and hence an object 100a. The medical provider 12 may in some aspects move the wand 300a along and/or across the body of the patient 18. For a detailed description of an exemplary interrogation and detection system, reference may be made to commonly owned U.S. Patent Application Publication No. 2004/0250819 to Blair et al., titled "Apparatus and Method For Detecting Objects Using Tags And Wideband Detection Device," filed Mar. 29, 2004, the entire contents of which is hereby incorporated by reference herein.

Figure 2:
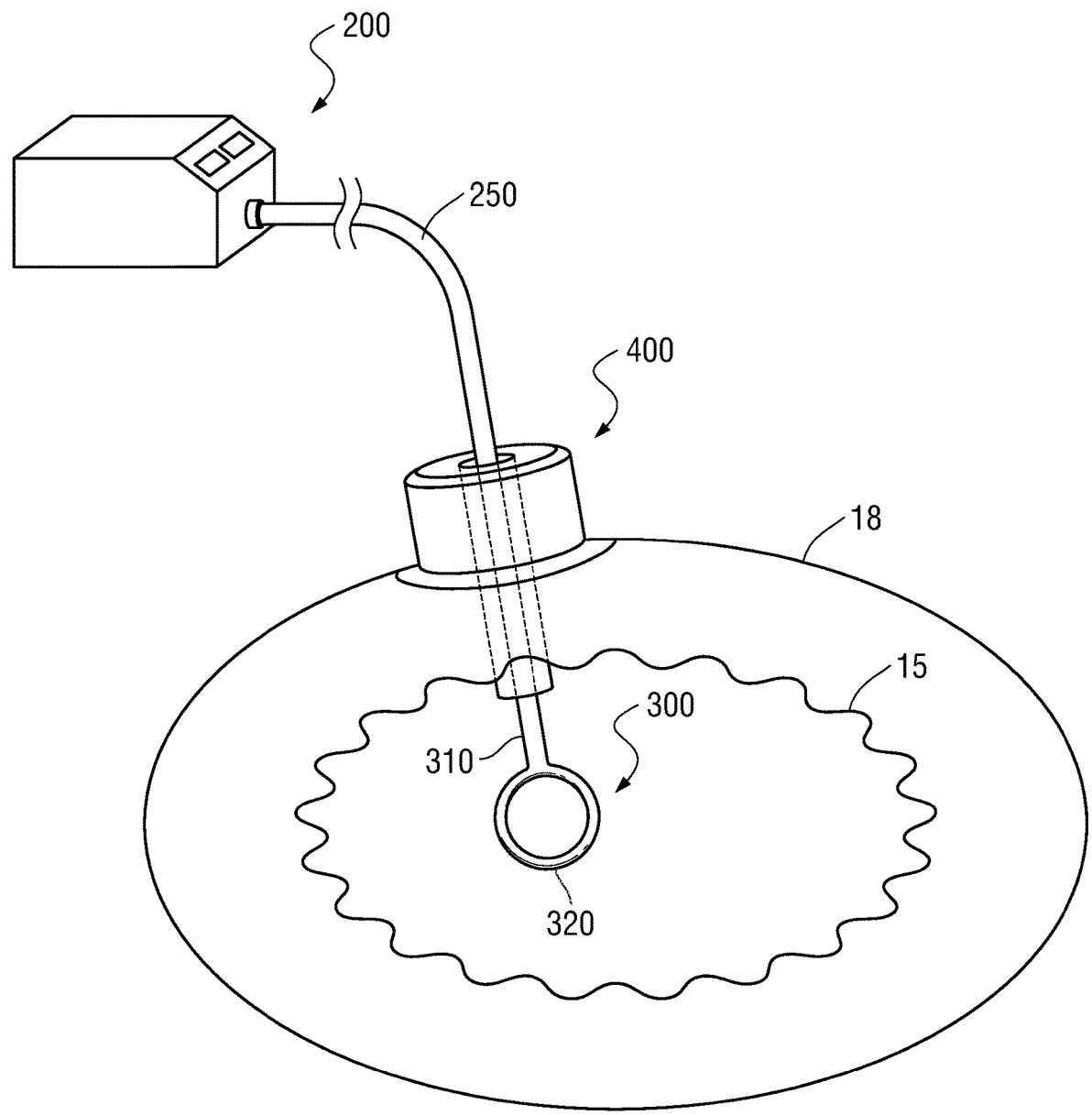
FIG. 2 is a schematic illustration of an in-vivo introducible antenna for detection of surgical implements within a patient's body in active use within a surgical site.

Referring now to FIG. 2, interrogation and detection system 10, for detection of surgical implements 100a within a patient's body, includes a signal generator 200 to provide an energizing signal for one or more RFID tags 100 (FIG. 1) affixed to an object 100a (FIG. 1). Each RFID tag is configured to transmit a return signal when energized, such that an antenna 300 can detect the return signal and confirm the presence of objects 100a within the body of patient 18. The antenna 300 is operably coupled to the signal generator 200 via a communication cable 250. Where the communication cable 250 may be of variable length to provide greater range of motion to the clinician handling the antenna 300.

In one aspect of interrogation and detection system 10, the antenna 300 is an in-vivo introducible antenna 300 includes a semi-rigid elongated member 310 supporting a flexible loop 320 configured to be inserted into surgical site 15 within the body of patient 18. Accordingly, interrogation and detection system 10 further includes a trocar-cannula assembly or port 400 to provide an access point for in-vivo introducible antenna 300 to be inserted into the body of patient 18. At a minimum, with reference to FIG. 2 trocar-cannula assembly 400 provides an elongated tubular channel 410 configured to facilitate the passage of in-vivo introducible antenna 300 therethrough. Further, a distal end of elongated tubular channel 410 must provide an open aperture 420 to grant the in-vivo introducible antenna 300 access to the surgical site 15 within the body of patient 18.

With additional reference to FIGS. 3A-F, in-vivo introducible antenna 300, as noted above, includes a semi-rigid elongated member 310 supporting a flexible loop 320 and must be inserted into a surgical site 15 within the body of patient 18. When free from the influence of external forces, flexible loop 320 occupies a region of space too large to be inserted through elongated tubular channel 410 or aperture 420 of trocar-cannula assembly 400, see FIGS. 4A and 4B. The increased size of flexible loop 320 is necessary to provide in-vivo introducible antenna 300 with a greater range of detection for return signals from RFID tagged objects within surgical site 15.

Figure 3A:
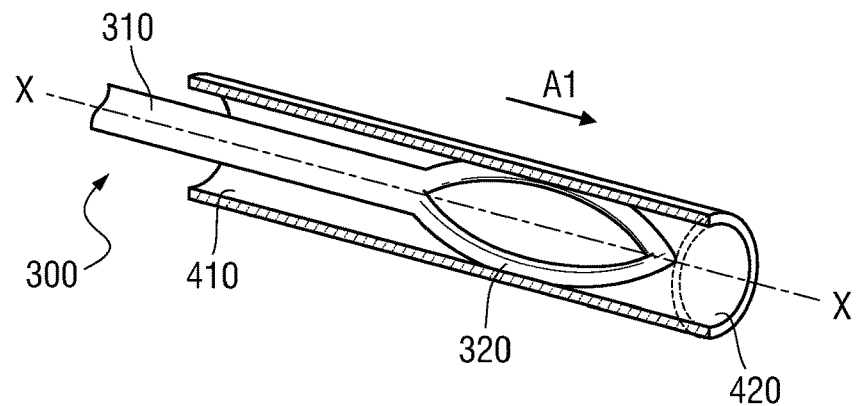
FIG. 3A is an enlarged perspective view of an in-vivo introducible antenna, in a compressed state, being pushed through a channel toward a surgical site within the patient's body.
Figure 3B:
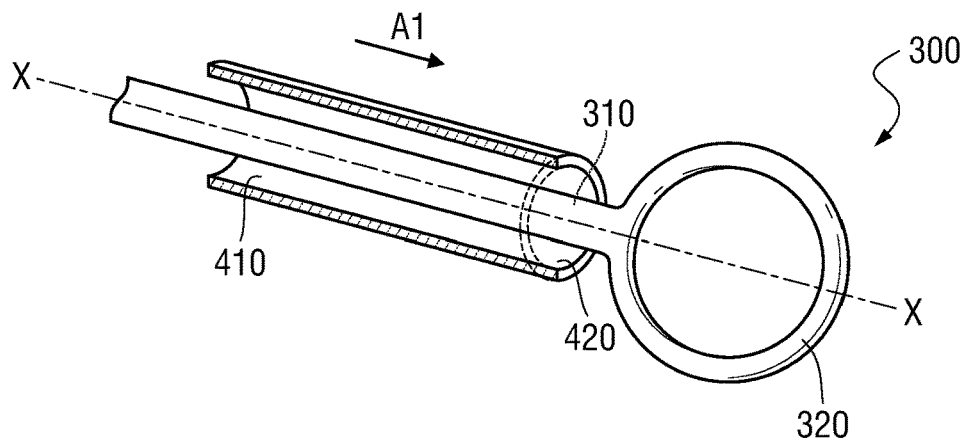
FIG. 3B is an enlarged perspective view of the in-vivo introducible antenna, in an expanded state, after being pushed through the channel of FIG. 3A and emerging into the surgical site within the patient's body.

In order to be inserted through elongated tubular channel 410 and aperture 420 of trocar-cannula assembly 400 without sacrificing the benefits of having increased size, flexible loop 320 of in-vivo introducible antenna 300 is composed of a shape memory alloy that is malleable enough to be compressed, folded, or otherwise reshaped to conform to its surroundings, while also being configured to automatically return to its original form when free from the influence of external forces. More specifically, the in-vivo introducible antenna 300 may be made from materials such as, nitinol, spring steel, silver, gold, copper, and various alloys of each listed material. In FIG. 3A, flexible loop 320 is initially circular in shape, but is compressed inward to form an elongated oval shape while being translated distally in direction "A1" through elongated tubular channel 410 toward the surgical site. Upon emerging through aperture 420 of elongated tubular channel 410 and entering the surgical site, flexible loop 320 automatically returns to its initial circular shape when free from the external influence of elongated tubular channel 410, as shown in FIG. 3B. Note, in other aspects the initial shape of flexible loop 320 may be non-circular, for example tear drop-shaped or oval.

Figure 3C:
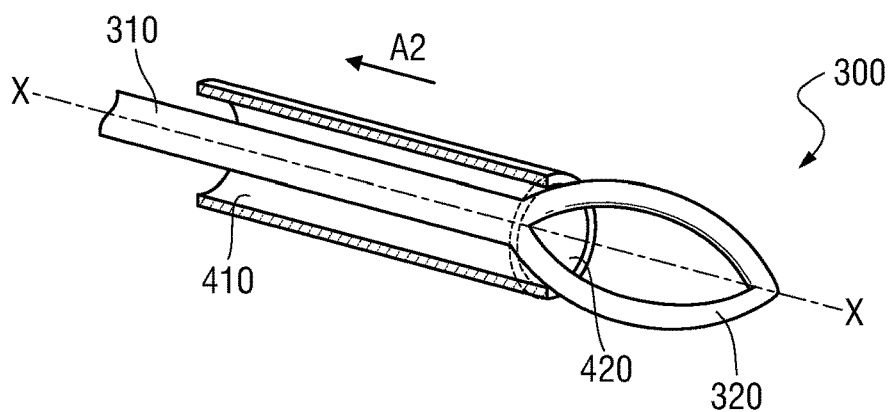
FIG. 3C is an enlarged perspective view of an in-vivo introducible antenna being withdrawn from a surgical site within the patient's body.
Figure 3D:
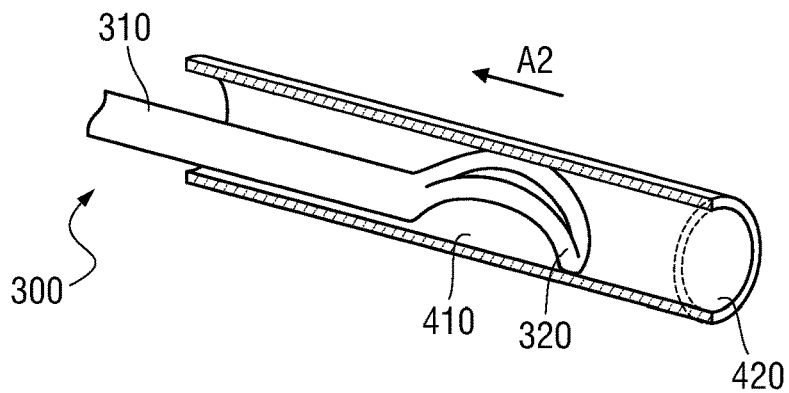
FIG. 3D is an enlarged perspective view of an in-vivo introducible antenna, in a folded state while being withdrawn from a surgical site within the patient's body.
Figure 3E:
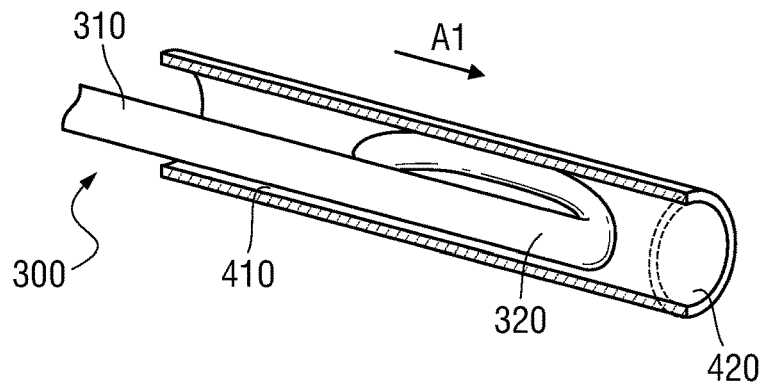
FIG. 3E is an enlarged perspective view of an in-vivo introducible antenna folded backwards while being pushed through a channel toward the surgical site within the patient's body.
Figure 3F:
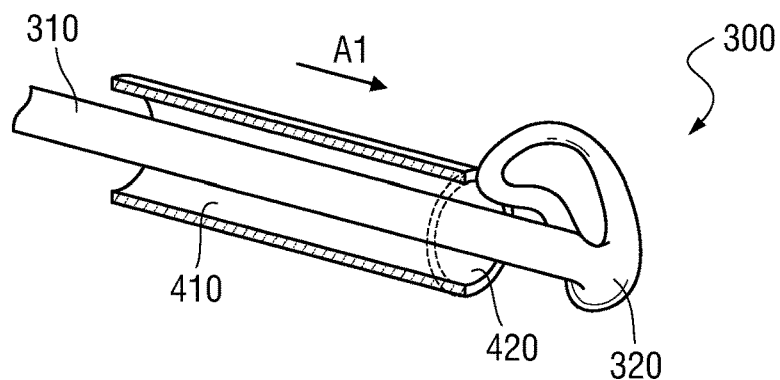
FIG. 3F is an enlarged perspective view of the in-vivo introducible antenna in a partially unfolded and expanded state, after being pushed through the channel of FIG. 3E and emerging into a surgical site within the patient's body.

In some aspects, flexible loop 320 can be folded along a longitudinal axis of semi-rigid elongated member 310 to form a crescent shape while being translated proximally in direction "A2" through elongated tubular channel 410 away from the surgical site as shown in FIGS. 3C and 3D. In still other aspects, the flexible loop 320 can be folded backward to rest alongside the semi-rigid elongated member 310 in addition to being compressed inward to form an elongated oval shape while being translated distally in direction "A1" through the tubular channel 410, only to automatically unfold and return to its original circular shape when free from the external influence of elongated tubular channel 410 upon emerging through aperture 420 and entering the surgical site, as shown in FIGS. 3E and 3F.

Now referring to FIGS. 4A-D, as noted above, in-vivo introducible antenna 300 occupies a region of space too large to be inserted through elongated tubular channel 410 or aperture 420 of trocar-cannula assembly 400 when free from the influence of external forces.

Figure 4A:
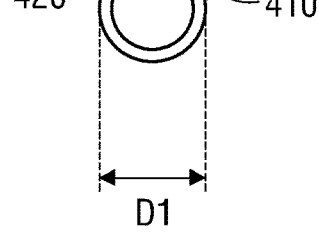
FIG. 4A is a frontal view of an elongated tubular channel and aperture thereof of the trocar-cannula assembly shown in FIG. 2.
Figure 4B:
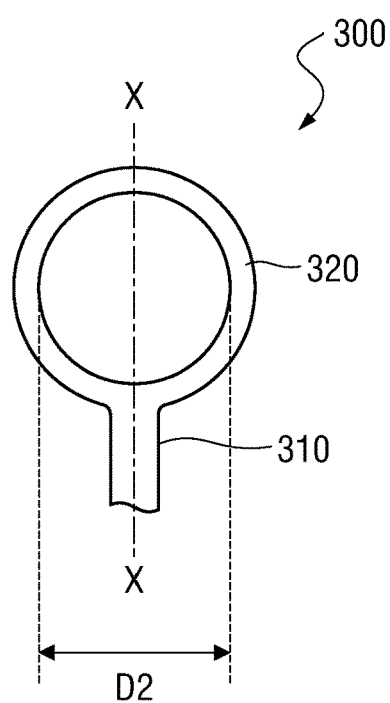
FIG. 4B is a profile view of the in-vivo introducible antenna of FIGS. 1-3F in its initial expanded state as shown in FIG. 3B.
Figure 4C:
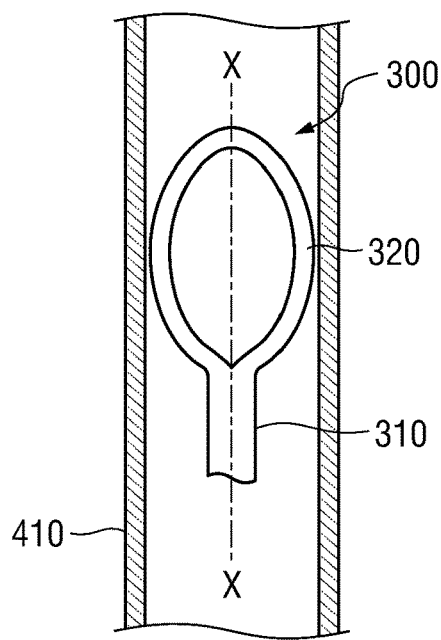
FIG. 4C is a profile view of the in-vivo introducible antenna compressed to form an elongated oval shape under the influence of the elongated tubular channel, as shown in FIG. 3A.
Figure 4D:
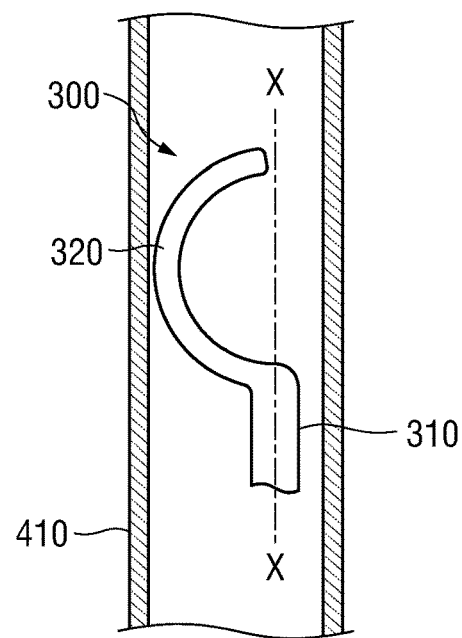
FIG. 4D is a profile view of the in-vivo introducible antenna folded to form a crescent shape under the influence of the elongated tubular channel, as shown in FIG. 3D.

FIG. 4A shows a frontal view of tubular channel 410, emphasizing that tubular channel 410 defines a generally circular shape having dimension or diameter "D1". Similarly, FIG. 4B shows a top view of in-vivo introducible antenna 300, wherein the flexible loop 320 defines a generally circular shape having dimension or diameter "D2" when measured transversely relative to longitudinal axis "X". Longitudinal axis "X" runs parallel to the direction of movement of in-vivo introducible antenna 300 within tubular channel 410, and therefore transverse measurement of dimension "D2" of flexible loop 32 presents a more accurate basis for comparing the relative sizes of tubular channel 410 and flexible loop 320. From FIGS. 4A and 4B, the dimensions "D1", "D2" of tubular channel 410 and flexible loop 320 show that "D2" is greater than "D1". Correspondingly, any measurement of size calculated based on dimensions "D1", "D2" will always show that flexible loop 320 is larger in size than tubular channel 410, thereby emphasizing the need for in-vivo introducible antenna 300 to be sizably adjustable in order to pass through elongated channel 410 and emerge out of aperture 420. FIG. 4C shows the elongated oval shape of flexible loop 320 due to compression forces exerted by the inner surface of elongated tubular channel 410 while being distally translated in direction, "A1" as shown in FIG. 3A. Similarly, FIG. 4D shows the crescent shape of flexible loop 320 as a result of being folded along longitudinal axis "X" of semi-rigid elongated member 310 while being proximally translated in direction "A2" through elongated tubular channel 410, as shown in FIG. 3D.

While aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. An interrogation and detection system for detection of surgical implements within a patient's body, comprising:
   one or more RFID tags configured to transmit one or more return signals when energized, each RFID tag affixed to a surgical implement within the patient's body;
   a remote signal generator configured to generate an energizing signal for the one or more RFID tags; and
   an in-vivo introducible antenna operably coupled to the signal generator, the in-vivo introducible antenna configured to receive the one or more return signals transmitted by the one or more RFID tags when in an expanded state,
   wherein the in-vivo introducible antenna is configured to a collapsed state, smaller than the expanded state, for insertion into the patient's body,
   wherein the in-vivo introducible antenna includes a semi-rigid elongated member supporting a flexible loop, wherein the flexible loop is configured to be folded proximally to rest alongside the semi-rigid elongated member.

2. The system of claim 1, further comprising:
   a trocar-cannula assembly including a tubular channel configured to facilitate passage of the in-vivo introducible antenna therethrough,
   wherein the in-vivo introducible antenna defines a shape having a dimension "D2"; and
   wherein the tubular channel defines a shape having a dimension "D1", such that the dimension "D1" of the tubular channel is less than the dimension "D2" of the in-vivo introducible antenna.

3. The system of claim 2, wherein the flexible loop is configured to fold proximally when passing through the tubular channel of the trocar-cannula assembly, and to unfold upon exiting the tubular channel of the trocar-cannula assembly and entering a surgical site within the patient's body.

4. The system of claim 3, wherein the flexible loop is composed of a shape memory alloy configured to automatically return to its initial shape in the absence of external forces.

5. The system of claim 4, wherein the initial shape of the flexible loop portion of the in-vivo antenna is circular.

6. The system of claim 5, wherein the flexible loop is configured to be folded inward to form an elongated oval shape while being translated distally through the tubular channel.

7. The system of claim 5, wherein the flexible loop is configured to be folded along an axis of the semi-rigid elongated member to form a crescent-shaped profile while being translated proximally through the tubular channel.

8. The system of claim 5, wherein the flexible loop is tear drop-shaped.

9. The system of claim 2, wherein the flexible loop is larger in size than the tubular channel.

10. A method for detecting one or more surgical implements within a patient's body, comprising:
    pushing an in-vivo introducible antenna distally through a channel having a dimension "D1" defined within a trocar-cannula assembly and into a surgical site within the patient's body, wherein the trocar-cannula assembly includes a tubular channel, and wherein a portion of the in-vivo introducible antenna is configured to fold proximally,
        wherein the portion of the in-vivo introducible antenna will automatically return to an original shape having a dimension "D2", such that the dimension "D1" of the tubular channel is less than the dimension "D2" of the in-vivo introducible antenna;
    generating an energizing signal configured to stimulate the one or more RFID tags into transmitting a return signal;
    transmitting the energizing signal directly into the surgical site within the patient's body through the expanded portion of the in-vivo introducible antenna;
    scanning for any return signals from one or more RFID tags affixed to each surgical implement placed within the patient's body before a commencement of surgery; and
    alerting a clinician to a presence of the one or more RFID tags affixed to each surgical implement upon detection of the one or more return signals.

11. The method of claim 10, wherein the in-vivo introducible antenna includes of a semi-rigid elongated member supporting a flexible loop, where the flexible loop is the portion of the in-vivo introducible antenna configured to automatically unfold to occupy an expanded area.

12. The method of claim 11, further including:
    pulling the unfolded flexible loop portion of the in-vivo introducible antenna proximally through an aperture and channel of the trocar-cannula assembly such that the unfolded flexible loop is compressed by the channel and folds proximally.

13. The method of claim 12, wherein the compression of the flexible loop portion facilitates complete withdrawal of the in-vivo introducible antenna from the trocar-cannula assembly.

14. The method of claim 13, wherein the flexible loop portion is circular in shape and is further configured to fold along an axis of the semi-rigid elongated member to form a crescent-shaped profile while being pulled proximally through the channel of the trocar-cannula assembly.

15. A resizable in-vivo introducible antenna for insertion into a surgical site and detection of RFID tagged surgical implements within a patient's body, comprising:
- a semi-rigid elongated member configured to be translated through a tubular channel,
  - wherein the tubular channel defines a shape having a dimension "D1"; and
- a flexible loop operably coupled to the semi-rigid member,
  - wherein the flexible loop defines a shape with a dimension "D2", such that the dimension "D1" of the tubular channel is less than the dimension "D2" of the in-vivo introducible antenna, and wherein the flexible loop is configured to deflect longitudinally relative to the semi-rigid elongated member.

16. The antenna of claim 15, wherein the flexible loop is composed of a shape memory alloy configured to automatically return to an initial shape in the absence of external forces.

17. The antenna of claim 16, wherein the flexible loop is sizably adjustable such that the flexible loop can be reshaped to conform to its surroundings.

18. The antenna of claim 17, wherein the initial shape of the flexible loop is a circle.

19. The antenna of claim 17, wherein the flexible loop is configured to be folded backwards to rest alongside the semi-rigid elongated member while being inserted into the surgical site within the patient's body.

* * * * *